(12) United States Patent
Foss et al.

(10) Patent No.: US 6,841,244 B2
(45) Date of Patent: Jan. 11, 2005

(54) ANTI-MICROBIAL FIBER AND FIBROUS PRODUCTS

(75) Inventors: Stephen W. Foss, Rye Beach, NH (US); Robert V. Sawvell, Jr., Columbia, SC (US)

(73) Assignee: Foss Manufacturing Co., Inc., Hampton, NH (US)

(*) Notice: Subject to any disclaimer, the term of this patent is extended or adjusted under 35 U.S.C. 154(b) by 0 days.

(21) Appl. No.: 10/770,306

(22) Filed: Feb. 2, 2004

(65) Prior Publication Data

US 2004/0197553 A1 Oct. 7, 2004

Related U.S. Application Data

(62) Division of application No. 09/565,138, filed on May 5, 2000, now Pat. No. 6,723,428.
(60) Provisional application No. 60/181,251, filed on Feb. 9, 2000, provisional application No. 60/180,536, filed on Feb. 7, 2000, provisional application No. 60/180,240, filed on Feb. 4, 2000, provisional application No. 60/173,207, filed on Dec. 27, 1999, provisional application No. 60/172,285, filed on Dec. 17, 1999, provisional application No. 60/172,533, filed on Dec. 17, 1999, and provisional application No. 60/136,261, filed on May 27, 1999.

(51) Int. Cl.[7] .................................................. D01F 8/00
(52) U.S. Cl. ........................ 428/370; 428/373; 428/374
(58) Field of Search ............................... 428/370, 373, 428/374

(56) References Cited

U.S. PATENT DOCUMENTS 3,589,956 A * 6/1971 Kranz et al. ................. 264/115
4,019,844 A    4/1977 Shiokawa et al.
4,350,006 A    9/1982 Aozawa et al.
4,525,410 A * 6/1985 Hagiwara et al. ............ 428/198
4,775,585 A * 10/1988 Hagiwara et al. ............ 428/323
6,037,057 A * 3/2000 Hartzog et al. ............. 428/373

FOREIGN PATENT DOCUMENTS

| JP | 01-14321 A | 1/1989 |
| JP | 07-145514 A | 6/1995 |
| JP | 10-60740 A | 3/1998 |

* cited by examiner

*Primary Examiner*—N. Edwards
(74) *Attorney, Agent, or Firm*—Perkins Smith & Cohen; Jerry Cohen; John A. Hamilton

(57) ABSTRACT

An anti-microbial and/or anti-fungal synthetic fiber that comprises various thermoplastic polymers and additives in a bi-component form in either a core-sheath or side-by-side configurations. The anti-microbial synthetic fibers comprise inorganic anti-microbial additives, distributed in certain areas to reduce the amount of the anti-microbial agents being used, and therefore the cost of such fibers. The fibers can incorporate anti-microbial additives so that they are not removed by repeating washing in boiling water and in dry clean cycles and become ineffective and conversely enhance access to the additives by washing or the like. The fibers comprise high tenacity polymers (e.g. PET) in one portion and hydrolysis resistance polymers (e.g. PCT) in another portion with the additives. The fibers can further be blended with non-anti-microbial fibers such as cotton, wool, polyester, acrylic, nylon etc. to provide anti-microbial finished fabrics. In one such embodiment, binder fibers are used which are mixed with other fibers.

15 Claims, 7 Drawing Sheets

FIG. 1B"

ANTI-MICROBIAL FIBER AND FIBROUS PRODUCTS

CROSS-REFERENCE TO RELATED APPLICATIONS

The present application is a divisional application of Ser. No. 09/565,138 filed May 5, 2000 now U.S. Pat. No. 6,723,428 which claims the priority of the following provisional applications: Ser. No. 60/136,261, filed May 27, 1999; Ser. No. 60/173,207, filed Dec. 27, 1999; Ser. No. 60/172,285, filed Dec. 17, 1999; Ser. No. 60/172,533, filed Dec. 17, 1999; Ser. No. 60/180,536, filed Feb. 7, 2000; Ser. No. 60/181,251, filed Feb. 9, 2000; and Ser. No. 60/180,240, filed Feb. 4, 2000.

FIELD OF THE INVENTION

The present invention relates generally to fiber, and, more particularly to a fiber having anti-microbial (and/or anti-fungal) properties which remain with the fiber when used in a fabric product after repeated launderings/uses. More specifically it provides a wholly or partly synthetic fiber and multi- or mono-component anti-microbial and/or anti-fungal synthetic fibers, alone or integrated with other synthetic or natural fibers, using various thermoplastic polymers and additives. It may be a bi-component fiber having either a core-sheath or side-by-side configuration or other configurations (e.g. pie-wedge). One arrangement uses binder fibers, which are staple fibers or filaments.

BACKGROUND OF THE INVENTION

There is a growing interest today in products which have anti-microbial and anti-fungal properties. There are a number of additives, fibers and products on the market which claim to have these properties. However, many do not have such properties, or the properties do not remain for the life of the product, or they have adverse environmental consequences.

Various materials have been used in the past to provide anti-microbial and anti-fungal properties to fibers and fabrics.

Examples of some organic types of anti-microbial agents, are U.S. Pat. Nos. 5,408,022 and 5,494,987 (an anti-microbial polymerizable composition containing an ethylenically unsaturated monomer, a specific one-, di- or tri-functional anti-microbial monomer and a polymerization initiator which can yield an unreleasable anti-microbial polymer from which the anti-microbial component is not released), 5,709,870 (a silver containing anti-microbial agent which comprises carboxymethylcellulose, a crosslinked compound, containing silver in the amount of 0.01 to 1% by weight and having a degree of substitution of carboxymethyl group of not less than 0.4 and the anti-microbial agent being a silver salt of carboxymethylcellulose, which is insoluble to water), 5,783,570 (an organic solvent-soluble mucopolysaccharide consisting of an ionic complex of at least one mucopolysaccharide and a quaternary phosphonium, an anti-bacterial antithrombogenic composition comprising organic solvent-soluble mucopolysaccharide and an organic polymer material, an antibacterial antithrombogenic composition comprising organic solvent-soluble mucopolysaccharide and an inorganic antibacterial agent, and to a medical material comprising organic solvent-soluble mucopolysaccharide).

Examples of some inorganic types of anti-microbial agents are:

Japanese Patent No. 1246204 (1988) which discloses an anti-microbial thermoplastic article with copper a compound added to the melted polymer just before extruding, in which the anti-microbial material is said to be resistant to washing.

U.S. Pat. No. 5,180,585 which discloses an antimicrobial with a first coating providing the antimicrobial properties and a second coating as a protective layer. A metal having antimicrobial properties is used including silver which is coated with a secondary protective layer.

Japanese Patent No. 2099606 (1990) which discloses a fiber with anti-microbial properties made of a liquid polyester and inorganic micro particles of zinc silicate, both being added to the melted polymer after polymerization and just before extrusion.

The use of anti-microbial agents in connection with thermoplastic material is known from U.S. Pat. No. 4,624,679 (1986). This patent is concerned with the degradation of anti-microbial agents during processing. This patent states that thermoplastic compounds which are candidates for treatment with anti-microbial agents include material such as polyamides (nylon 6 or 6,6), polyvinyl, polyolefins, polyurethanes, polyethylene terephthalate, styrene-butadiene rubbers.

Japanese Patent No. 2091009 (1990) and U.S. Pat No. 5,047,448 disclose an anti-microbial thermoplastic polymer with copper or zinc compounds and fine particles of Al, Ag, Fe and Zn compounds and a liquid polyester, in which the anti-microbial material is said to be resistant to washing.

Japanese Patent No. 2169740 (1990) discloses a thermoplastic fiber such as PET which uses silver, copper or zinc as an anti-microbial agent. There is a cellulose component which reduces the amount of thermoplastic with anti-microbial agent and reduces the cost.

Examples of inorganic types of anti-microbial agent which have zeolite with silver is disclosed in U.S. Pat. Nos. 4,911,898, 5,094,847, 4,938,958 (use of zeolite with exchangeable ions such as silver and others), 5,244,667 (an anti-microbial composition which involves use of partial or complete substitution of ion-exchangeable metal ion such a silver, copper, zinc and others), 5,405,644 (an anti-microbial fiber having a silver containing inorganic microbiocide and the silver ion is stated to have been supported by zeolite, among other materials, the purpose being to prevent discoloration).

Various products have been made using anti-microbial fibers. U.S. Pat. No. 5,071,551 discloses a water purifier having a secondary filter downstream of its primary filter for removing microorganisms and antimicrobial means disposed between the two filters. use of an anti-microbial agent for a water purifier.

Japanese Patent No. 6116872 (1994) discloses a suede-like synthetic leather with an anti-microbial agent. It discloses the use of anti-microbial zeolite having an anti-microbial metal ion. It uses two fiber types and includes PET.

U.S. Pat. No. 5,733,949 discloses an anti-microbial adhesive composition for dental use. The composition was made by blending of a polymerizable monomer having alcoholic hydroxy group and water to a dental composition containing an anti-microbial polymerizable monomer and a polymerizable monomer having acidic group, and with a polymerization catalyst. Such composition has capability to improve adhesive strength between the tooth and the restorative material to prevent microbial invasion at the interface and kill microorganisms remaining in the microstructure.

U.S. Pat. No. 5,876,489 discloses a germ-removing filter with a filter substrate and an anti-microbial material dispersedly mixed into the filter substrate. The anti-microbial material is an ion exchange fiber bonded with silver ion. In the ion exchange fiber, silver ions capable of killing living germs through an ion exchange reaction.

U.S. Pat. No. 5,900,258 discloses a method for preventing a microorganism from growing and the breakdown of urea to ammonia on the surface of skin, wall, floor, countertop or wall covering, or in absorbent materials by incorporating an effective amount of naturally-occurring and/or synthetic zeolites. The absorbent materials are diapers, clothing, bedsheets, bedpads, surgical apparel, blankets, filters, filtering aids, wall coverings, countertops, and cutting boards, etc. Use of zeolite preventing bacterial infections and rashes in mammals may compromise cell wall processes including basic transport processes. Zeolites may capture or neutralize electrons and inhibit electron transport through key enzymes of the electron transport chain such as cytochrome oxidase.

U.S. Pat. No. 6,037,057 is for a bi-component fiber in which the cross sectional area of the sheath is less than 28% of the total cross sectional area. It also discloses the use of a slickening agent and use of an anti-microbial agent which is an inert inorganic particle having a first coating with the anti-microbial properties, and a second coating which has protective properties.

One of the disadvantages of some of the prior art is that the anti-microbial additives are organic and many organic materials either act as antibiotics and the bacteria "learns" to go around the compound, or many of them give off dioxins in use.

Also, many such additives are applied topically to the fibers or fabrics and tend to wash off or wear off over time and become ineffective. Also, by washing off the additives are placed into the waste water stream.

There are many patents and other published information which are available concerning garments and other articles intended for use for incontinent persons. Many of these deal with the problem of moving body fluids away from a person's skin to prevent the type of problems created when such fluids remain in contact with the skin for long periods of time, such as rashes and other skin eruptions. Absorbent layers are provided behind the layer which touches the skin.

However, there is the danger of infection due to bacterial and fungal growth in urine-soaked fabrics and the overall discomfort caused by wet clothing.

There has been little attention to a problem which remains even when the fluids are moved away from the skin. This is the problem caused by microbes which attach to the outer layer which touches the skin even when the fluids move into the absorbent layer. These microbes cause a variety of problems.

The University of Minnesota Extension Service, Waste Education Series published an article in 1998, "Infant Diapers and Incontinence Products: Choices for Families and Communities by Gahring et al relating to this subject (hereafter "UOM Article"). This article indicates that the use of disposable diapers and incontinence products have been widely adopted for babies and for adults with certain problems. There is an estimate that there are at least ten million adult Americans who are incontinent. One of the problems is rashes and skin irritation.

Moisture absorbing incontinence products are produced in various manners including plastic film or coated nylon for a waterproof backing, paper fiber, gelling material, or cotton gauze; flannel for a middle absorbent layer and nonwoven or woven or knitted fabrics made of polyester, olefin, viscose or cotton for the coverstock.

This article discusses health issues for babies relating to the condition of the skin and to the transmission of infectious diseases. Prolonged contact with urine and stool is a major cause of diaper rash.

There are environmental problems associated with the large use of disposable products of this type. And this will increase as the number of elderly people in our society increases. While disposables are placed into landfills together with other trash, it appears that many people do not empty the contents of disposables into the toilet, and a study has shown that diaper wastes represent a significant health hazard in landfills. While many such products claim to be biodegradable, this is not always correct and there is some difficulty in making the moisture impervious layers of the plastics used in such products, biodegradable.

Also it has been found that super-absorbent disposable diapers are more effective than cloth diapers with separate waterproof pants/wraps. The transmission of infectious disease is a major concern for care, outside of the home. The fecal containment of disposable diapers is found to be significantly better than that of cloth diapers with plastic pants.

Vehicle and aircraft cabin air filters are vulnerable to the seeding of bacteria and fungi from outside air sources and air conditioning systems, thus providing hospitable sites for their inhibited growth. The latter is especially true since these filters often recirculate cooled air from air-conditioners. Thus, these materials would benefit from having antibacterial and anti-fungal agents incorporated into them. However, most prior art approaches of coating fibers or materials with anti-microbial or anti-fungal agents have limited effect.

There have been complaints about the "musty air" smell which is notices when air conditioning equipment is turned on in such cabins. This smell is caused by the growth of mold and bacteria with the air conditioning system.

There exists a need to develop fabrics and other effective material for use in air filters for vehicle and aircraft cabins that do not cause the development of resistant bacterial strains. There also still exists a need for these filters to have substrates-anti-microbial agent systems that are resistant to being washed away, thus maintaining their potency as an integral part of the filters into which they are incorporated.

U.S. Pat. No. 5,876,489, mentioned above, describes use of a cation exchange to provide a fiber bonded with silver ions, usable in a germ removing filter for sterilizing air for a sterile room such as is used in the manufacture of food products. A problem with using silver zeolite fine particles for such a filter is that the particles fall out and generate dust, thereby deteriorating the function of a HEPA filter with which it is used. When other methods are used in which the zeolite particles are two microns, with fiber filament having a diameter of 8–15 microns, insufficient zeolite particles are available on the surface of the synthetic fiber filament.

Wound care dressings can introduce pathogens that increase the danger of infection due to bacterial and fungal growth into the wound tissue because it is necessary to changing these dressings frequently. As a result of the constant re-exposure of the healing wound to the air, the dressings used to cover these wounds are suitable for the use of anti-microbial and anti-fungal fibers during their manufacture. In addition, the use of these anti-microbial materials could allow these dressings to be used for longer periods of time before they need to be changed or even to possibly be reusable, although they are usually considered disposable after one use. However, most prior art approaches of coating such fibers or fabrics with anti-microbial or anti-fungal agents have had limited success.

Burn dressings are used to prevent infection due to high potential for introducing bacteria and other pathogens into the burn tissue due to the fact that the normal protective barrier of the skin has been grossly disrupted. The possibility of bacterial and fungal growth in the burn tissue during healing is one of the major dangers to recovery. Also, as a result of the constant re-exposure of the healing burn tissue to the air during the changing of dressings, the materials used to protect these burns are suitable for the use of anti-microbial and anti-fungal fibers during their manufacture. In addition, the use of these anti-microbial materials could allow these burn dressings to be used for longer periods of time before they need to be changed.

Several patents describe anti-microbial materials in which the anti-microbial agent is resistant to being washed away. Similarly, U.S. Pat. No. 4,919,998 (1990) discloses an anti-microbial medical fabric material for use in surgical gown and scrub suits, sterilization wrappers and similar material that retains its desirable properties after repeated institutional launderings.

U.S. Pat. No. 4,226,232 discloses a wound dressing which provides many desirable properties. However, there is only brief mention of the use of anti-microbial agents, and there is no discussion of providing such agents onto the surface of the fibers contacting the wound to provide the best efficacy of anti-microbial agents.

U.S. Pat. No. 5,098,417 for a cellulosic wound dressing with an active agent ionically absorbed thereon has the anti-microbial or anti-fungal agent applied to an already prepared fabric.

U.S. Pat. No. 5,147,339 for a dressing material for the treatment of wounds has an anti-microbial applied to the already formed fabric as a coating.

U.S. Pat. No. 5,219,325 for a wound dressing has a top layer and a lower layer (which contacts the wound) connected together by a fibrous layer. The lower layer has an anti-microbial applied after the layer is formed.

Thus, there still exists a need to develop metal-containing anti-microbial agents that do not cause the development of resistant bacterial strains for incorporation into fibers that are used to make a variety of materials. There also still exists a need for these anti-microbial agents to be resistant to being abraded or washed away, thus maintaining their potency as an integral part of the fibers into which they are incorporated.

PETG as used herein means an amorphous polyester of terephthalic acid and a mixture of predominately ethylene glycol and a lesser amount of 1,4-cyclohexanedimethanol. It is known that PETG can be used in polycarbonate blends to improve impact strength, transparency, processability, solvent resistance and environmental stress cracking resistance.

Udipi discloses in U.S. Pat. Nos. 5,104,934 and 5,187,228 that polymer blends consisting essentially of PC, PETG and a graft rubber composition, can be useful as thermoplastic injection molding resins.

Chen et al. in U.S. Pat. No. 5,106,897 discloses a method for improving the low temperature impact strength of a thermoplastic polyblend of PETG and SAN with no adverse effect on the polyblends clarity. The polyblends are useful in a wide variety of applications including low temperature applications.

Billovits et al. in U.S. Pat. No. 5,134,201 discloses that miscible blends of a thermoplastic methylol polyester and a linear, saturated polyester or co-polyester of aromatic dicarboxylic acid, such as PETG and PET, have improved clarity and exhibit an enhanced barrier to oxygen relative to PET and PETG.

Batdorf in U.S. Pat. No. 5,268,203 discloses a method of thermoforming thermoplastic substrates wherein an integral coating is formed on the thermoplastic substrate that is resistant to removal of the coating. The coating composition employs, in a solvent base, a pigment and a thermoplastic material compatible with the to-be-coated thermoplastic substrate. The thermoplastic material, in cooperation with the pigment, solvent and other components of the coating composition, are, after coating on the thermoplastic substrate, heated to a thermoforming temperature and the thermoplastic material is intimately fused to the thermoplastic substrate surface.

Ogoe et al. in U.S. Pat. No. 5,525,651 disclose that a blend of polycarbonate and chlorinated polyethylene has a desirable balance of impact and ignition resistance properties, and useful in the production of films, fibers, extruded sheets, multi-layer laminates, and the like.

Hanes in U.S. Pat. No. 5,756,578 discloses that a polymer blend comprising a monovinylarene/conjugated diene black copolymer, an amorphous poly(ethylene terephthalate), e.g. PETG, and a crystalline poly(ethylene terephthalate), e.g. PET, has a combination of good clarity, stiffness and toughness.

Eckart et al. in U.S. Pat. No. 5,958,539 disclose a novel thermoplastic article, typically in the form of sheet material, having a fabric comprising textile fibers embedded therein. The thermoplastic article is obtained by applying heat and pressure to a laminate comprising an upper sheet material, a fabric comprised of textile fibers and a lower sheet material. The upper and lower sheet materials are formed from a co-polyester, e.g. PETG. This thermoplastic article may be used in the construction industry as glazing for windows. One or both surface of the article may be textured during the formation of the articles.

Ellison in U.S. Pat. No. 5,985,079 discloses a flexible composite surfacing film for providing a substrate with desired surface characteristics and a method for producing this film. The film comprises a flexible temporary carrier film and a flexible transparent outer polymer clear coat layer releasably bonded to the temporary carrier film. A pigment base coat layer is adhered to the outer clear coat layer and is visible there through, and a thermo-formable backing layer is adhered to the pigmented base coat layer. The film is produced by extruding a molten transparent thermoplastic polymer and applying the polymer to a flexible temporary carrier thereby forming a continuous thin transparent film. The formed composite may be heated while the transparent thermoplastic polymer film is bonded to the flexible temporary carrier to evaporate the volatile liquid vehicle and form a pigment polymer layer. The heating step also molecularly relaxes the underlying film of transparent thermoplastic polymer to relieve any molecular orientation caused by the extrusion. Ellison also mentions that it is desirable to form the flexible temporary carrier from a material that can withstand the molten temperature of the transparent thermoplastic polymer. The preferred flexible temporary carriers used in his invention are PET and PETG.

Currently, many tee shirts, such as the grey athletic shirts, are made by blending in up to 10% of either solution dyed black polyester or stock dyed cotton. The solution dyed polyester has a disadvantage in that the product can no longer be labeled 100% cotton. The stock dyed cotton has the disadvantage in that it is not color fast, especially to bleach, and that it needs to be passed through a dye bath.

While anti-microbial agents are known in the footwear art, the agents used in these applications are generally organic substances. The disadvantage of these organic agents when used as anti-microbial agents is that bacteria can develop a resistance to their action. Thus, one is faced with the emergence of bacterial strains that are no longer affected by these anti-microbial agents which negates the function of these materials, and is harmful to humans since they are resistant to antibiotics.

A variety of patents relate to anti-microbial materials being added to materials. For example, U.S. Pat. No. 3,959,556 (1976) relates to synthetic fibers that incorporate an anti-microbial agent. U.S. Pat. No. 4,624,679 (1986), mentioned above, uses anti-microbial agents in connection with thermoplastic materials. These materials are formed by mixing polyamide resins, anti-microbial agents, and an antioxidant for reducing the degradation of the anti-microbial agent at the high temperatures necessary for processing.

Several other patents describe anti-microbial materials in which the anti-microbial agent is resistant to being washed away. U.S. Pat. No. 4,919,998 (1990) discloses an anti-microbial material that retains its desirable properties after repeated washings.

However, these materials have two inherent commercial disadvantages. First, while the anti-microbial agents incorporated into them do show some resistance to repeated washings, these agents do leach out of the materials, primarily because they are not physically incorporated into them. In fact, in many cases, the anti-microbial agents are only loosely bound into the material and are relatively easily washed away or naturally abraded away over time.

On the other hand if the agents are buried too deeply in the material or homogeneously distributed they will not contact microbes at all and the economics of usage will be adversely affected.

Second, the anti-microbial agents used in these applications are generally organic substances. The disadvantage of these agents when used as anti-microbial agents is that bacteria can develop a resistance to their action. Thus, one is faced with the emergence of bacterial strains that are no longer affected by these anti-microbial agents which negates the function of these materials.

U.S. Pat. No. 4,923,914 for a Surface-Segregatable, Melt-Extrudable Thermoplastic Composition discloses forming a fiber or film of polymer and an additive in which the additive concentration is greater at the surface. for example when surfactants are added to polymers to impart a special property thereto such as a hydrophilic character to the surface, if the additive is compatible with the polymer there is a uniform concentration of the additive throughout the polymer. In the past such webs have been bloomed to bring the surfactant to the surface. But the surfactant is incompatible at melt-extrusion temperatures. The patentee describes a process for overcoming this problem.

However, the process described has not been very usable with anti-microbial agents. For example, see U.S. Pat. No. 5,280,167 which describes the '914 patent discussed above and states that previous attempts to apply the teachings thereof to the preparation of non-woven webs having anti-microbial activity were not successful. This '167 patent provides for delayed anti-microbial activity in order to delay the segregation characteristic of the '914 patent from occurring. The additive which is used is a siloxane quaternary ammonium salt, an organic material.

While these anti-microbial agents are designed to prevent the development of resistant bacterial strains, the use of metal-containing materials presents the added difficulty of being able to successfully disperse the anti-microbial agents throughout the material. Since these metal-containing compounds exists as fairly large size particles (10 microns and greater), the ability to evenly mix or distribute them is limited. In addition, because of this size problem, these substances must necessarily be applied to the surfaces of materials instead of being incorporated into them. The latter causes the additional disadvantage of making the applied anti-microbial agents relatively labile to washings or abrasion.

Thus, there still exists a need to develop anti-microbial non-woven sheet material and fabrics for various uses that do not cause the development of resistant bacterial strains. There also still exists a need for these filters to have substrates-anti-microbial agent systems that are resistant to being washed away, thus maintaining their potency as an integral part of the filters into which they are incorporated.

U.S. Pat. No. 4,350,732 for reinforcing laminate which issued Sep. 21, 1982 discusses a moldable laminate which could be molded into curved shapes and which is bondable to a carrier surface and which is useful in the making of military boots and the like. The present invention is an improvement.

Institutional furnishings are subject to excessive wear and tear. These furnishings must withstand the constant onslaught of dirt and spills of a variety of substances. They must also stand up to frequent cleanings with industrial strength cleansers. As a result, these furnishings could be made stronger and more resistant by using anti-microbial and anti-fungal agents in their manufacture. The limited prior art approaches of coating fibers and/or fabrics with anti-microbial or anti-fungal materials have had only limited success.

Home furnishings are not subjected to as much wear and tear as institutional furnishings and are usually made of a material which has a softer "feel" and is usually more delicate than those made for institutional use. Therefore, it is difficult to make such materials which will stand up to repeated washings and to wear, particularly when they have been prepared with additives for special properties such as anti-microbial agents.

U.S. Pat. No. 3,983,061 for a process for the permanent finishing of fiber materials, including carpets, discloses an aqueous acid liquid for finishing fiber materials especially dyed carpets to make them anti-static, dirt-repellent, and optionally anti-microbial using a single bath process for finishing dyed textile floor coverings to make provide these characteristics to them. It states that the properties are "permanent" and defines this to mean retaining the properties after a "prolonged" period of wear and tear. However, the anti-microbial properties are not believed to last sufficiently long to be of commercially useful application, and the anti-microbial agent disclosed is organic in nature.

U.S. Pat. No. 4,371,577 for an anti-microbial carpet containing amino acid type surfactant is incorporated into fibrous materials prior to or after fabrication into a carpet using an organic material. The fibrous materials can be polyamide acrylic, polyester or polypropylene fibers. The preparation is accomplished in two manners. The first is that the pile yarns, the carpet foundations or the yarns for carpet foundation are subjected to the impregnation treatment with a surfactant, and the other is that a carpet fabricated from fibrous materials is impregnated with an organic material.

U.S. Pat. No. 5,762,650 for a biocide plus surfactant for protecting carpets where the dyeing and anti-microbial finishing is performed simultaneously. The anti-microbial agent is an organic material.

While there are known anti-microbial agents which are said to be designed to prevent the development of resistant bacterial strains, the use of metal-containing materials presents the added difficulty of being able to successfully disperse the anti-microbial agents throughout the fibers. Since these metal-containing compounds exist as fairly large size particles (10 microns and greater), the ability to evenly mix or distribute them is limited. In addition, because of this size problem, these substances must necessarily be applied to the fibers instead of being incorporated into them. The latter causes the additional disadvantage of making the applied anti-microbial agents relatively labile to washings.

Thus, there still exists a need to develop fabrics, materials and surfaces substrates for use in home and institutional furnishings which contain metal-containing anti-microbial agents that do not cause the development of resistant bacterial strains for incorporation into fibers that are used to make a variety of fabrics. There also still exists a need for these anti-microbial agents to be resistant to being washed away, thus maintaining their potency as an integral part of the fibers, fabrics, materials, and furnishings into which they are incorporated.

Medical wipes are used for a variety of cleaning and disinfectant purposes in hospital and other institutional settings. Even though most current materials of this kind are disposable, their use increases the potential of moving pathogens from surface to surface. Any spreading of these pathogens increases the possibility of bacterial and fungal growth on a variety of surfaces, which can lead to the transmission of infectious materials, particularly in institutional settings. Thus, the materials used in medical wipes are amenable to the incorporation of anti-microbial and anti-fungal fibers during their manufacture. By using these anti-microbial materials, medical wipes could be used for longer periods of time before they need to be changed. However, most prior art approaches of coating fibers or fabrics with anti-microbial or anti-fungal agents have had limited success.

U.S. Pat. No. 5,709,870 (1998), mentioned above, discloses a silver-containing anti-microbial agent that has good affinity to the fiber and is stable to heat and light. The anti-microbial consists of silver bound to carboxymethylcellulose in the amount of 0.01 to 1.0 percent silver by weight that is applied to the fibers.

While these anti-microbial agents are designed to prevent the development of resistant bacterial strains, the use of metal-containing materials presents the added difficulty of being able to successfully disperse the anti-microbial agents throughout the fibers. Since these metal-containing compounds exists as fairly large size particles (10 microns and greater), the ability to evenly mix or distribute them is limited. In addition, because of this size problem, these substances must necessarily be applied to the fibers instead of being incorporated into them. The latter causes the additional disadvantage of making the applied anti-microbial agents relatively labile to washings.

Thus, there still exists a need to develop metal-containing anti-microbial agents that do not cause the development of resistant bacterial strains for incorporation into fibers that are used to make a variety of materials. There also still exists a need for these anti-microbial agents to be resistant to being abraded away, thus maintaining their potency as an integral part of the fibers into which they are incorporated. In the event they are not disposable, they need to be resistant to washings.

SUMMARY OF THE INVENTION

It is an object of the present invention to provide an anti-microbial fiber in which the anti-microbial agents are efficacious and adhere to the fiber and are greatly resistant to washing off or wearing off of the fiber or fabric to which they are applied.

It is also an object of the present invention to provide an anti-microbial fiber in which the anti-microbial additives are inorganic.

It is another object of the present invention to provide a fiber with anti-microbial properties in which the anti-microbial agent is applied to certain areas, or has higher concentrations in certain areas, to reduce the amount of the anti-microbial agent which needs to be used and thus lower the cost of such fiber and/or a fabric including such fiber.

It is another object of the present invention to provide an anti-microbial fiber combined with non-anti-microbial fibers for use in anti-microbial finished fabrics that are able to withstand significant wear and washings and still maintain their effectiveness.

It is a further object of the present invention to provide an anti-microbial fiber:
  combined with color pigments for coloration for the use in anti-microbial finished fabrics to withstand fading;
  combined with UV additives to withstand fading and degradation in fabrics exposed to significant UV light;
  combined with additives to make the surface of the fiber hydrophilic or hydrophobic;
  combined with additives to make the fabric flame retardant or flame resistant;
  combined with additives to make the fabric anti-stain; and/or using pigments with the anti-microbial so that the need for conventional dyeing and disposal of dye materials is avoided.

These and other objects of the present invention are accomplished by synthetic fibers having anti-microbial and/or anti-fungal properties using various thermoplastic polymers blended with other types of fibers, and additives, some incorporating natural fibers.

Thus, the present invention provides a synthetic anti-microbial fiber comprising high and low levels of various thermoplastic polymers and controlled concentrations of inorganic anti-microbial additives mixed with polymers and selectively placed in the end product for greatest technical effectiveness and cost effectiveness.

The anti-microbial and/or other agent(s) are held in the sheath and are exposed externally by suitable sizing of particle cubes and sheath thickness, e.g., using one micron cubes and 2 micron thick sheaths, and similar ratios of sheath to core in other sizes.

The present invention also provides a synthetic anti-microbial fiber comprising high tenacity polymers e.g. polyesters, polyethylene terephalate (PET) in one portion and hydrolysis resistance polymers in another portion with hydrophilic and anti-microbial additives. In some applications the latter portion can be deliberately made hydrolysis-vulnerable to allow "blooming" and enhanced access to anti-microbial additives in the course of several washings or extended uses.

Also, the present invention provides an anti-microbial finished fabric by blending the synthetic anti-microbial fibers with non-anti-microbial fibers such as cotton, wool, polyester, acrylic, nylon, and the like.

The various polymers, include but are not limited to, polyethylene (PE), polypropylene (PP), polyethylene terephthalate (PET), PCT, PETG [PET, type G], Co-PET and copolyesters generally, Styrene, polytrimethylene terephalate (PTT)m 3GT, Halar®, polyamide 6 or 6,6, etc. The additives include pigments, hydrophilic or hydrophobic additives, anti-odor additives and anti-microbial/anti-fungal inorganic compounds, such as copper, zinc, tin and silver.

PETG is an amorphous binder fiber which can be blended into yarns with other fibers to form fabrics, as well as non-woven fabrics. After heat activation, the PETG fiber melts, wets the surface of the surrounding fibers, and settles at the crossing points of the fibers, thus forming "a drop of glue" which bonds the fibers together and distributes the anti-microbial additives.

The excellent wetting characteristics of PETG can be used to distribute the anti-microbial additive uniformly within a yarn or fabric. In addition to the zeolite of silver, the PETG could carry other inorganic anti-microbial additives such as copper, zinc, or tin.

In addition to the anti-microbial component, the invention may be used to carry pigments with the PETG to achieve certain colors without the need to dye the other fibers.

The created synthetic fibers of polymers and additives can further be blended with non anti-microbial fibers to provide anti-microbial finished fabrics that are able to withstand significant wear and washings and maintain their effectiveness.

The use of hot water improves the products in that washing the fibers/products in hot water opens the pores of the PET and such washed products perform better than unwashed products (this is thought to be due to the removal of spinning/weaving lubricants).

Material can be made in biodegradable form, such as by adding corn starch to the core or sheath polymers. This enables whole families of disposable fibers and fabrics.

Use of a cloth diaper and a garment over it is effective, especially when antimicrobial/anti-fungal fibers are used for the fibers which have contact with the waste matter, although beneficial effects are available even when the anti-microbial/anti-fungal agents are used only in the fibers which touch the body.

Due to the urine soaking which occurs with incontinent persons, these garments are suitable for the use of anti-microbial and anti-fungal fibers during their manufacture. The use of such anti-microbial material allows these garments to be reusable without the negative effects of present reusable garments of this type. The anti-microbial may be fabric (knitted or woven) plus absorbent pads. This also applies to bed packs for bed ridden patents to prevent bed sores.

The garments and articles intended for use for incontinent persons have anti-microbial and/or anti-fungal fibers in a woven or non-woven fabric of the garment or article which is in contact with such person's skin to eliminate or substantially reduce the problems caused by such microbes. Such garments and articles may be cleaned and reused many times while maintaining the beneficial anti-microbial qualities thereof.

The foregoing objects are met by anti-microbial fibers that have been designed using inorganic silver-containing compounds that allow the formation of both mono- and multi-component polymeric fibers having these anti-microbial agents intermixed within the polymer during fiber formation. The concentration of the anti-microbial agent can be varied within each individual fiber as a gradient using mixing strategies and also from fiber to fiber. The concentration of anti-microbial agent within a fabric or material made from these anti-microbial fibers can also be varied regionally using fibers containing varying amounts of anti-microbial agents in conjunction with both natural and synthetic fibers having different amounts of anti-microbial agents or even no added anti-microbial agents. A variety of other agents can be added, either by mixing or topically, to color the fibers and/or to make it resistant to staining, fire, and ultraviolet (UV) light as well as altering its water absorbing qualities. Various polymers, without limitation, can be used to form these fibers. In the context of this invention, anti-microbial refers, but is not limited, to anti-bacterial and anti-fungal.

FIG. 10 shows a wound care dressing 52 which includes a bottom layer 46, a top layer 48 and an intermediate absorbent fibrous layer 50 which joins the other two layers. The bottom layer 46 is used directly against the wound and therefore the fibers of this layer have the anti-microbial agent applied thereto as described below.

The invention provides fibers with silver zeolite as a component that may be woven, knit, non-woven or employed in other fabric types and may be used with any variety of natural or synthetic fibers in addition to the anti-microbial fibers.

These objects and others are accomplished in accordance with the present invention which uses PETG:

As a carrier for pigments for coloration for use in finished fabrics to withstand fading;

With pigments together with other fibers, so that the need for conventional dyeing and disposal of dye materials is avoided;

With pigments and other fibers, and the resulting fabric possesses excellent fastness for both sunlight resistance and washing;

With pigments for coloration, the color of the fabric remains fast for in excess of 50 commercial launderings;

With pigments blended with cotton, which leaves the encapsulated pigment attached to the outside of the cotton fiber and ceases to be a fiber after activation, so that the resulting fabric can still be labeled 100% cotton fiber; and With anti-microbial and/or other additives with any natural fibers, so that the resulting fabrics have anti-microbial and/or other properties with the same characteristics of natural fabrics.

PETG may be used as one of the polymer blends and/or carriers for a wide variety of applications. PETG is an amorphous binder fiber that can be blended into yarns with other fibers to form woven fabrics, as well as knits and non-woven fabrics. It has two characteristics of particular interest: (1) excellent wetting and (2) low melting temperature (which can be controlled between 90° C. and 160° C.). It is used in the present invention as a carrier to carry pigments and/or anti-microbial additives and/or other additives and is blended with other fibers which may be natural fibers such as cotton, silk, flax, wool, etc. or other synthetic fibers such as: PET, PP, PE, Nylon, Acrylic, etc. After heat activation, the PETG melts, continuously releases the color pigments and/or anti-microbial or other additives and wets the surface of the surrounding fibers with the pigment and/or anti-microbial or other additives it carries. It settles at the crossing points of the fibers, thus forming "a drop of glue" which bonds the fibers together. Therefore, PETG delivers and distributes the pigments and/or anti-microbial or other additives uniformly within a fabric, generating the finished fabrics and/or fabrics having anti-microbial properties.

Since the natural fibers used to blend with PETG are not changed physically after heat activation of PETG, they contain the same characteristics as natural fibers. The PETG may be used together with or without anti-microbial agents to form a fabric having excellent color fastness even in the presence of sunlight, and will withstand many washings without deterioration. The fabric is made by blending PETG used as a carrier for pigments and/or anti-microbial additives, with cotton or any other fibers of synthetic material such as from polyester and rayon, and activating PETG from 110° to 140° C. The color is thus provided to the yarn and fabric without the need of going through a dye bath. This fabric remains color-fast for in excess of 50 commercial launderings.

The excellent wetting characteristics of PETG can be used to distribute the pigments and/or anti-microbial additive uniformly within a yarn or fabric. While many anti-microbial agents may be used, such as those, which use copper, zinc, or tin, the preferred agent is zeolite of silver. In addition to the anti-microbial component and the pigment added to the PETG, the PETG may be used as a carrier to add other properties to yarn and fabric, such as fire retardants.

The product can be a nonwoven fabric of synthetic fibers, primarily polyester, but which could be acrylic, nylon, rayon, acetate, PP, and the like. The fabric can have a weight from 65–400 grams per square meter and typical fibers range from 1.2 dTex to 17 dTex with a cut length of 15–180 mm. They are carded, cross-lapped and needle punched, but could be produced on other types of nonwoven equipment, such as spun laced or spun bonded equipment.

The impregnation is a latex of SBR, vinyl acetate, PVC, acrylonitrile, and the like. Impregnation is from 1–4 times the weight of the nonwoven fabric on a dry basis. A range of fillers such as clay, calcium carbonate, and the like are used to reduce the cost. There are two basic methods. One is to mix the anti-microbial with latex compound and impregnate it.

A variety of other agents can be added, either by mixing or topically, to color the material and/or to make it resistant to staining, fire, and ultraviolet (UV) light as well as altering its water absorbing qualities. Various polymers, without limitation, can be used to form these fibers. In the context of this invention, anti-microbial refers, but is not limited, to anti-bacterial and anti-fungal.

The concentration of the anti-microbial agent can be varied within each individual fiber as a gradient using mixing strategies and also from fiber to fiber. The concentration of anti-microbial agent within a fabric or material made from these anti-microbial fibers can also be varied regionally using fibers containing varying amounts of anti-microbial agents in conjunction with both natural and synthetic fibers having different amounts of anti-microbial agents. A variety of other agents can be added, either by mixing or topically, for different reasons, such as altering its water absorbing qualities. Various polymers can be used to form these fibers. In the context of this invention, anti-microbial refers, but is not limited, to anti-bacterial and anti-fungal.

BRIEF DESCRIPTION OF THE DRAWING

Other objects, features and advantages will be apparent from the following detailed description of preferred embodiments taken in conjunction with the accompanying drawings in which.

DESCRIPTION OF PREFERRED
EMBODIMENTS OF THE INVENTION

In the United States, all claims concerning anti-microbial and anti-fungal properties must be thoroughly tested to Environmental Protection Agency (EPA) and Food and Drug Administration (FDA) standards before making claims. The anti-microbial herein can be said to "kill bacteria" in that it kills 99.99% (log 4) of bacteria in 24 hours, and "anti-microbial" in that is kills 99.9% (log 3) of bacteria in 24 hours. This is based upon actual test results. Testing, such as by using the shake flask test, has demonstrated that when fibers and fabrics are tested using the anti-microbial system disclosed herein, the number of bacteria on the fibers is reduced by 99.99% or more over a 24-hour period and at least by 99.9%. This testing was performed using several different bacteria, including *Pseudomonas aeruginosa, Staphylococcus aereus* and *Klebsiella pneumoniae*. The testing was conducted using both unwashed fibers and fibers that had been washed fifty times to simulate use of the fiber in an application, such as a pillow. The EPA has indicated that products tested using this system may claim "Prohibits Bacteria Growth and Migration Along the Surface of the Product." The addition of the agent in this system inhibits the growth of mold and mildew or odor-causing bacteria in the fibers. This is a true anti-microbial product. The fibers retain their efficacy after simulated use conditions so that the anti-microbial action lasts the life of the product.

THE FIBERS AND THE ADDITIVES

Figure 1A:
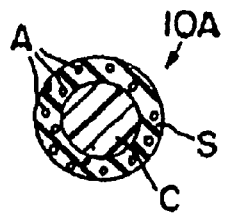
FIGS. 1A, 1B, 1B', 1B" and 1C are cross-sectional views of various fiber configurations used in practice of the various embodiments of the invention.
Figure 1B:
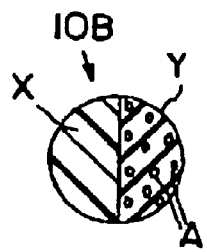
Figure 1B:
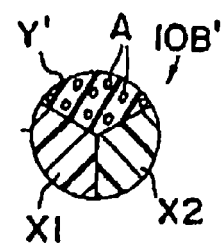
Figure 1C:
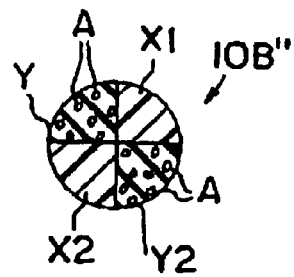
Figure 1C:
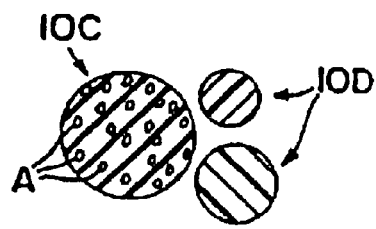
Figure 2:
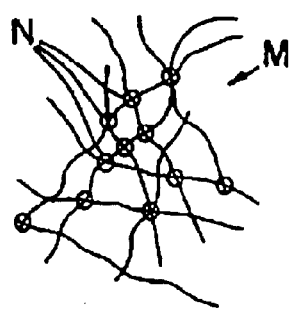
FIG. 2 is a sketch of a fibrous mass using one or more of the fibers of FIGS. 1A–1C.

According to a first configuration of the present invention shown in FIGS. 1A–2 a bi-component fiber 10A is formed of a sheath component S and a core component C using polyethylene terephthalate (PET) (or other thermoplastic polymer) in the core, making up between 20 to 80% of the fiber by weight. The sheath is also PET, or other thermoplastic polymer, making up between 80 to 20% of the fiber by weight including, as a dispersed solid, additive A (or compounded with the sheath plastic) an anti-microbial compound, to gain the efficiency of the additive on the surface and not wasting the additive in the core.

In the more generalized case as mentioned above, the sheath may be quite thin. However, preferably the sheath is more than 28% of the total fiber cross-section. It has been found that one of the best methods for retaining the antimicrobial qualities in the fiber and in fabrics is to use sheath thicknesses which are properly related to the size of the anti-microbial additive particles. For example, when the anti-microbial particles are approximately 1 micron cubes, which provides diagonal dimensions of approximately 1.7 microns, the sheath thickness would be in the vicinity of 2 microns. In this manner the particles of the agent are firmly held in the sheath by the material of the sheath holding them in place. When the particles are larger or smaller, the thickness of the sheath is adjusted accordingly.

The anti-microbial/anti-fungal additives are inorganic compounds using such metals as: copper, zinc, tin, and silver. The best results are obtained using a zeolite of silver dispersed in a polyethylene (PE), PET, or polybutylene terephthalate (PBT) carrier, but could be added directly to a melt of a sheath thermoplastic without an intermediate carrier. The total anti-microbial additive ranges from 0.2% (0.002) to 6.0% (0.06) by weight of fiber depending on performance requirements. The anti-microbial additives are held in the sheath and are prevented from washing off over time and remain effective, especially when the sheath-thickness to agent-particle size ratio is in a desirable range as mentioned above and discussed in more detail below.

The bi-component anti-microbial/anti-fungal synthetic fiber size would preferably range from 0.7 dTex to 25.0 dTex and could be produced as a cut staple fiber in lengths from 1.0 mm to 180 mm, or in a continuous filament.

Additives which can be incorporated include one or more of UV stabilizers at 0.1% (all %'s herein are by weight unless otherwise stated) to 5.0%; fire retardant (FR) additives at 0.1% to 5.0%; pigments at 0.1% to 6.0%; hydrophilic additives at 0.2% to 5.0%; hydrophobic additives at 0.2% to 5.0%; and/or anti-stain additives at 0.2% to 5.0%.

A second configuration of this first embodiment of the present invention is a bi-component fiber 10B in which the components x, y (x=strength, y=functional portion) are side-by-side and the same polymers and additives are used as described above. Variants of this are shown in FIG. 1B' in which the tri-component fiber 10B' has components x1, x2 and y', and in FIG. 1B" in which the four-component fiber 10B" has components x1, x2, y1 and y2.

A third configuration shown in FIG. 1C is a continuous filament 10C that could be used by itself as the binder or as part of a yarn or fabric with cooperating (strength) fibers indicated at 10D.

It should be understood that the nominal "binder" fiber or binder component can also be a strength enhancer in some combinations. It will also be understood that other variants with respect to FIGS. 1A–1C, including, but not limited to combinations, can be made. For example, a first extrusion could produce intermediate fiber products as in FIG. 1A and such products could be put together with each other or separate strength fibers and processed to produce simulations of FIGS. 1B, 1B'. 1B", 1C.

FIG. 2 shows a non-woven or woven fibrous mass M made up of any of the fibrous configurations of FIGS. 1A–1C after heating wherein the binder fiber component melts and flows to form locking knots at many (if not most or all) of the cross-over points or nodes N of the fibrous mass to enhance strength and durability of the mass while maintaining a dispersion of the binder materials and its functional additive(s).

While the preferred embodiment is a PET/PET bi-component with zeolite of silver being used only in the sheath. Resins with different viscosities can be used to obtain improved performance. A PCT/PET arrangement is one variation which takes advantage of the hydrolysis resistance and resilience; however, the PET/PET is more cost effective, especially for use in apparel and bedding.

FIGS. 1A–2 can also be used to describe a second embodiment grouping of practice of the invention.

The first configuration of the second embodiment of the present invention is a bi-component fiber of a core and a sheath as shown in FIG. 1A using PET or other high tenacity polymer in the core at between 20% and 80% by weight of the fiber. Poly 1,4 cyclohexylene dimethylene terephthalate (PCT) or other hydrolysis resistant polymer is used for the sheath at 80% to 20%. The core is designed to provide the strength of the fiber and the modulus can be varied to create a high modulus fiber with properties of high tenacity and low elongation similar to cotton, or a low tenacity and higher elongation fiber with properties similar to wool; or anywhere in between to obtain different fibers to make them as compatible as possible for their end uses and for any blend in which they will be used. In fibers, modulus refers to the area under the curve in a stress/strain curve. The sheath is preferably over 28% of the total cross sectional area. The sheath uses PCT which provides a hydrolysis resistant surface with good wrinkle resistance and resistance to long term washings in boiling water and strong soaps.

Additives in this second embodiment include pigments, compounds to create a hydrophilic surface, and anti-microbial, anti-fungal, anti-odor additives. The pigment additives are to provide uniform colors that do not fade significantly over long-term use and washing, unlike dyes. Compounds may be used which create a hydrophilic surface and this is designed to wick body moisture away from the skin and evaporate to create comfort for a wearer of a garment containing such fibers and is particularly useful for career apparel such as uniforms, work clothes, etc. The anti-microbial, anti-fungus and anti-odor additives can be varied depending on the functionality of the career apparel.

The bi-component anti-microbial/anti-fungal synthetic fiber size ranges from 0.7 dTex to 25.0 dTex and can be produced as a cut staple fiber in lengths from 1.0 mm to 180 mm, or in a continuous filament.

Another arrangement (FIG. 1C) is a bi-component continuous filament that could be used by itself or as part of a yarn or fabric.

FIGS. 1A–2 can also be used to describe a third embodiment grouping of practice of the invention.

The third embodiment of the invention is a mono-component of homo-polymer fiber made from low temperature polymers with a melting or softening temperature below 225° C. such as PETG. It relates to a binder fiber carrier for anti-microbial additives, which can be further blended with non-anti-microbial fibers to provide an anti-microbial finished fabric that is able to withstand significant wear and washings and maintain their effectiveness. The anti-microbial additives are inorganic.

A mono-component or homo-polymer fiber used in this embodiment was made from low temperature polymers with a melting or softening temperature below 225° C. such as PETG (PET modified with 1,4, cyclohexanedimthanol), PE, PP, co-PET, or amorphous PET. Another low melting temperature polymer which may be used is polycaprolactam (PCL). The anti-microbial additives are inorganic compounds made from metals such as copper, tin, zinc, silver, etc. The preferred compound is a zeolite of silver dispersed in PE, PET, or PBT before being added to the fiber. The additives could be added directly to the primary polymer with pre-dispersion. The total active ingredients range from 0.1 to 20% by fiber weight. Other inorganic metals such as tin, copper, zinc, etc. work also but not as well as zeolite of silver.

The binder (carrier) fiber containing polymers and anti-microbial additives can be blended with non anti-microbial natural fibers such as cotton and wool, or synthetic fibers such as polyester, acrylic, nylon, PTT, 3GT, rayon, modified rayon, and acetate to an anti-microbial finished fabrics that is able to withstand significant wear and washings and maintain their effectiveness.

A typical example is a fiber using the PETG polymer with the zeolitic contained silver additive blended with cotton up to 10% by weight to produce a bed sheet. The binder fiber is activated in the drying cycle of the final bleaching operation or other heat operation. The PETG melts and wets the surface of the cotton fibers to carry the anti-microbial characteristics to the entire sheet with an added benefit of increasing strength and reducing pilling.

The fiber size ranges from 0.7 dTex to 25 dTex and a staple length of 1.0 mm to 180 mm. A continuous filament yarn can also be produced that can be used in a wrap spun application whereby non-anti-microbial fibers are spun around the anti-microbial filament The antimicrobial product withstands more than 50 commercial washings at 80° C. and/or dry cleanings. It is immune to UV exposure of at least 225 kj. It possesses excellent abrasion resistance and is unaffected by tests such as Tabor or Wyzenbeek.

The present invention also provides a unique way to use polymers such as PETG to carry and deliver anti-microbial additives and/or pigments to a natural non-anti-microbial fiber, such as cotton, wool, possibly mixed with polyester, nylon and the like, and generate a final binding fabric having anti-microbial properties.

PETG has two characteristics of interest: (1) excellent wetting and (2) low melting temperature. In the present invention, it is used as a carrier to carry anti-microbial additives and be blended with non-anti-microbial fibers. After heat activation, the PETG melts, continuously releases the anti-microbial additives and wets the surface of the surrounding non anti-microbial fibers with the anti-microbial additives it carries. Thus, PETG delivers and distributes the anti-microbial additive uniformly within a fabric and the PETG holds the anti-microbial agent in place, generating the finished fabrics having anti-microbial property. Since the natural fibers used to blend with PETG are not changed physically in this process, they contain the same characteristics as natural fibers.

The bi-component fiber may be formed by the use of pellets of the two different polymers or a direct polymer stream from the reactor of which the fiber is to be formed. The arrangement shown in FIG. 1A is intended for a configuration of a core fiber, and a sheath fiber which contains an additive, e.g., an anti-microbial agent. Since the best of the anti-microbial agents known at this time to the present inventor is zeolite of silver, the present example uses this agent. The intent is to use the minimum amount necessary to provide the desired characteristics. The additive provides the desired anti-microbial effect only at the surface. Therefore, if the bulk of the additive is located within the volume of the fiber well below the surface, that portion will not be useful for most or all of the life of the material into which the fiber is made. Since there frequently is some surface abrasion, some of the additive particles which are just below the surface when the fiber is made, become available at the surface, later in the life of the product.

In the past, attempts have been made to provide the additive at the surface, and the result was that the additive particles did not have a very useful life since they were removed from the surface by washing and wear or use. Therefore, the present invention strongly attaches the additive particles to the outer region of the fiber.

It has been possible to make particles of zeolite of silver as small as 1 micron cubes. A particle of such size will have a diagonal dimension of about 1.7 micron. Therefore, the smallest thickness of the sheath would be about 2 microns. The present invention permits a, core/sheath arrangement in which the sheath is as small as 2 microns in thickness with the additive incorporated into the sheath. The diameter of the sheath is adjusted to the particle size so that the particles are held firmly in place and are available at the surface of the sheath. The particles may be smaller or larger than 1 micron cubes or larger, and the sheath may be correspondingly smaller than 2 microns or larger. In such an arrangement most, or all, of the additive is available for surface action, and, with wear and/or washings a small amount of the surface of the sheath will wear or wash away, and other additive particles which were originally more deeply embedded, become available at the surface.

Figure 5:
FIGS. 5 and 6 are photomicrographs of fibers showing the particles of zeolite of silver.
Figure 6:
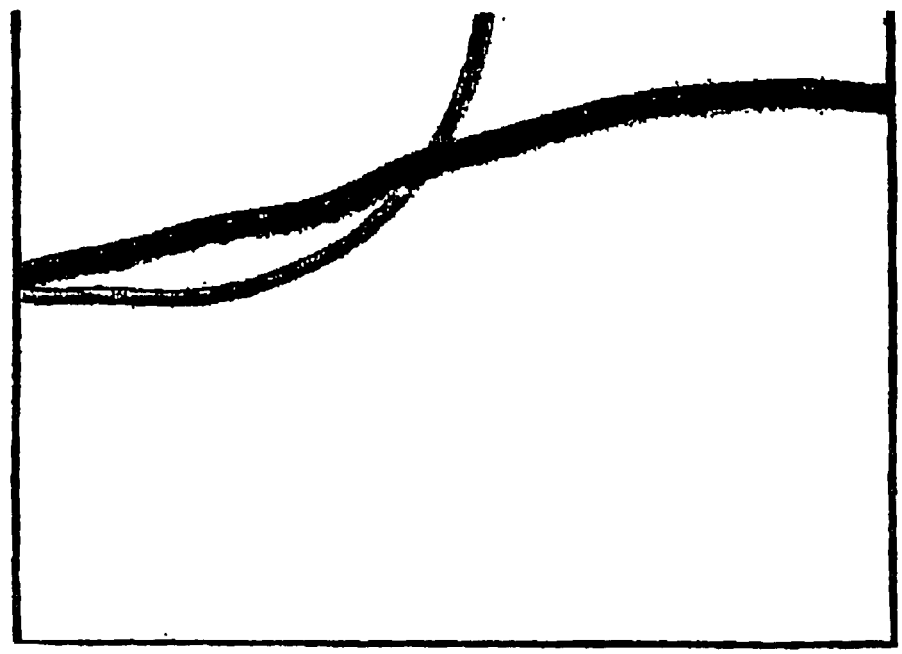

The photomicrographs of FIGS. 5 and 6 show the small particles of zeolite of silver in the sheath, many of which can be seen on the surface or projecting through to the surface of the fibers. There are more such particles which are just below the surface of the fibers, and which will become available for anti-microbial activity as small portions of the fiber wears or washes away and the particles become available at the surface.

Figure 4:
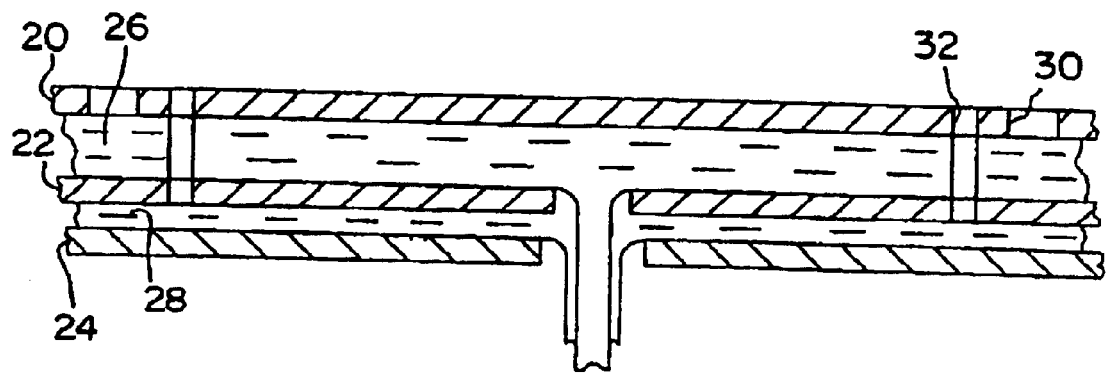
FIG. 4 is a sectional view through the exit of the extruder showing the formation of coaxial bi-component fibers of the present invention.
Figure 3:
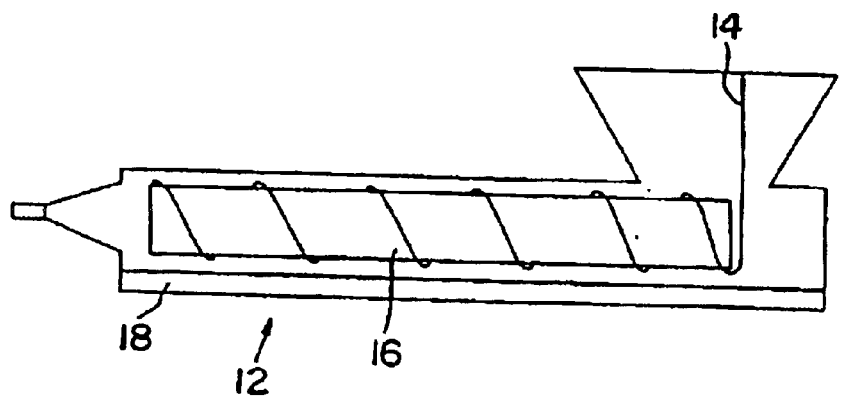
FIG. 3 is a schematic view of the feed hopper, screw and extruder.

FIGS. 3 and 4 show a manner of making a core/sheath fiber with an anti-microbial additive which is incorporated into the sheath polymer prior to the final extruding of the fiber. In the prior art, this was mostly done as a treatment after extruding.

The extruder 12 is shown diagrammatically in FIG. 3 having a feed hopper 14, an extruder screw section 16 for feeding melted material to the delivery end, and a heating chamber 18 which surrounds the bottom of the feed hopper as well as the total length of the extruder screw section 16 for melting the pellets which are fed into the hopper and maintaining the polymers in melted condition for being extruding through the extruding openings which act as nozzles. Besides pellets, it is possible to make these fibers using direct polymer streams from continuous reactors feeding to the melt pumps for a company which is a polymer producer.

There are two extruders, one which has a feed hopper for forming the sheath and another with a hopper for forming the core.

The nozzle end of the extruder is shown in cross section in FIG. 4 which includes three sheets of metal 20, 22 and 24 to form two chambers 26 and 28. The melted polymer is fed into the extruder nozzle from the top. There are a plurality of two types of holes, one type being 28 and which feeds into chamber 26 to form the core of the fiber, and the other type being 32 which feeds into chamber 28 to form the sheath of the fiber.

The following non-limiting examples illustrate practice of the invention.

EXAMPLE 1

The anti-microbial fiber of the present invention was used in the making of a mattress pad. In this example, 15% of a 6.7 denier 76 mm cut length natural white fiber was used as a homofilament with zeolite of silver as the anti-microbial agent and 15% of a bi-component fiber was used together with 70% PET 6×3 T295 in a blend in which the zeolite of silver comprised 0.9% of the fiber. The blend of this fiber was made into a batt of about 1–1½" thickness of nonwoven material which was then placed between two layers of woven fabric to form a mattress pad. When tested using the shake flask test this provided a 99.99% microbial kill ratio.

There are other examples in which all of the parameters of Example 1 were used and in each of which there was 15% of a bi-component fiber used. Again the zeolite of silver comprised 0.9% of the fiber. The percentage of the anti-microbial fiber ranged from 20% to 40% and the PET ranged from 45% to 65%. In all examples the microbial kill ratio was 99.99% using the shake flask test.

EXAMPLE 1A

In this example, 35% of a 6.7 denier 51 mm cut length natural white fiber was used in a sheath/core bi-component configuration with zeolite of silver as the anti-microbial agent and 15% of another bi-component fiber was used together with 50% PET 6×3 T295 in a blend in which the zeolite of silver comprised 1.8% of the fiber. The blend was then prepared as in Example 1 and when tested using the shake flask test, there was a 99.9% microbial kill ratio.

A second group similar to the first one was prepared in which the sheath/core bi-component fiber with zeolite of silver as the anti-microbial agent comprised from 10 to 35% of the fiber blend, 15% of another bi-component fiber was used and from 50 to 75% of PET 6×3 T295 was used. The zeolite of silver comprised 0.75% of the fiber. In the shake flask test, there was a 99.99% microbial kill ratio.

EXAMPLE 2

In this example, 15% of a 3.5 denier 38 mm cut length PETG fiber was used as a homofilament with zeolite of silver as the anti-microbial agent. 85% PET fiber was blended with the PETG anti-microbial fiber to form a blend in which the zeolite of silver comprised 1.8% of the fiber. The fiber was made into a wall covering and was tested by the shake flask test, which provided a microbial kill rate of 99.99%

A modified version was prepared the same way except that there was only 10% fiber with zeolite of silver in the blend and 90% PET fiber was used. After the fiber was made into a wall covering, this too provided a 99.99% microbial kill rate using the shake flask method of testing.

A further modified version was used in which there was only 5% fiber having zeolite of silver in the blend and 95% PET fiber in the blend. The testing, after the fiber was used in a wall covering, again provided a 99.99% microbial kill rate for bacteria.

The fibers described above can be used to make both woven and nonwoven fabrics as well as knitted fabrics. Such fabrics are useful for various types of articles, some of which are listed below.

INCONTINENT GARMENTS

Incontinent garments, including disposable diapers, underwear, pajamas, and linens, some of which may be knitted. This is disclosed, for example, in pending provisional application Ser. No. 60/173,207 filed Dec. 27, 1999, the contents of which are physically incorporated herein below, in which garments and other articles for incontinent persons made of an anti-microbial fiber comprises various thermoplastic polymers and additives in a mono-component or bi-component form in either a core-sheath or side-by-side configurations. The anti-microbial synthetic fibers can comprise inorganic anti-microbial additives, distributed only in certain areas in order to reduce the amount of the anti-microbial agents being used, and therefore the cost of such fibers. The anti-microbial additives used in the synthetic fibers do not wash off over time because they are integrally incorporated into these fibers, thus their effectiveness is increased and prolonged. The anti-microbial synthetic fibers comprise high tenacity polymers (e.g. PET) in one component and hydrolysis resistance polymers (e.g. PCT) in another component. The hydrophilic and anti-microbial additives provide a hydrolysis-resistant surface with good wrinkle resistance that results in long-term protection against washings in boiling water and strong soaps. The anti-microbial synthetic fibers can further be blended with non-anti-microbial fibers such as cotton, wool, polyester, acrylic, nylon etc. to provide anti-microbial finished fabrics that are able to withstand significant wear and washings and while maintaining their effectiveness.

Anti-microbial fibers can be used to make materials for a variety of applications in which it is necessary or desirable to reduce bacterial and fungal growth and the resultant odor. Specifically, in personal hygiene situations, these materials can be used in reusable or re-wearable incontinent garments and other articles such as linens and bed packs to prevent bed sores on persons confined to bed for extended periods of time. Diapers and other clothing and articles for incontinent individuals are constantly and intermittently being soaked with urine and these items as now manufactured are not effective at killing odor and infection-causing bacteria. By making these items disposable, the growth of bacteria and fungi is reduced depending upon how often they are changed, but there are environmental and other considerations to disposables. However, the use of the anti-microbial fibers in such garments and articles that maintain their effectiveness during washings, results in reusable garments and articles of the type described with odor reducing and anti-microbial properties which last for the life of such garments and articles.

As a result of the above, the use of anti-microbial fibers in the manufacture of incontinent garments is desirable. These anti-microbial fiber-containing garments are useful in reducing the growth of bacteria, fungi, and other microbes once soaked with urine, thus reducing the discomfort of the individual and preventing infections generally. Specifically, the anti-microbial fiber-containing fabrics may be used in both the covering fabric and the water absorbent interior material. In this way, both surface and interior protection is achieved. In addition, these materials may also be made to be reusable because the anti-microbial effect of the fibers of these garments and articles are resistant to multiple washings. Thus, a significant cost savings is realized in the laundry operations of hospitals and nursing homes as well as in the economics of individual households.

In manufacturing these materials, any of the fiber embodiments described below could be used. Both the strength and resiliency of these materials is important since they must stand up to multiple wettings and subsequent cleanings. Thus, both bi-component fibers and mixed fiber fabrics are useful embodiments for incontinent garments. Also, other modifications of the characteristics of these fibers and fabrics beyond that of adding anti-microbial agents, including the addition of agents to increase or decrease hydrophobicity, are useful in view of the repeated wettings and the need for frequent cleanings and washings. In addition, anti-odor additives may be particularly useful in this application in light of this frequency of cleaning, as well as the wetting with urine. Thus, these anti-microbial materials, garments and articles significantly reduce the growth of mold, mildew, and bacteria in home and institutional environments.

Garments for incontinent persons are made of anti-microbial fibers designed to use inorganic silver-containing compounds that are integrated into the polymers that are used to make these anti-microbial fibers. However, other metals (such as copper, potassium, magnesium, and calcium) can be used as anti-microbial agents. In addition, mixtures of different metal-containing anti-microbial agents in differing concentrations can be used that result in hybrid agents tailored for specific tasks.

Such garments may be knitted or woven and include underwear, pajamas, linens, disposable diapers, and the like.

Figure 7:
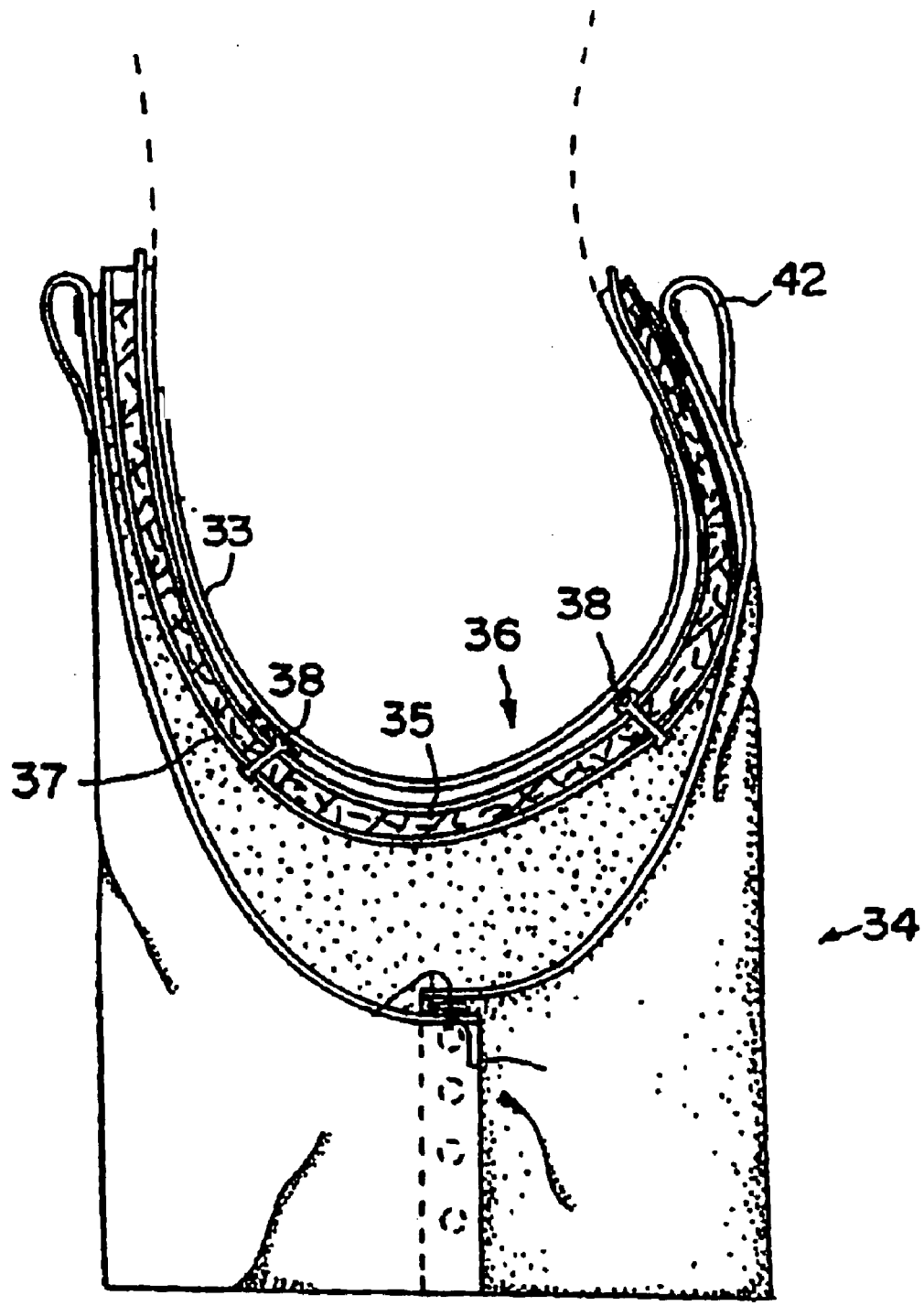
FIG. 7 shows a garment made from the fibers of the present invention for a person who is incontinent.

One type of such garment of the present invention is shown in FIG. 7 in which there is a garment 34 which carries a removable liner assembly 36 which is detachably secured within the garment. The liner assembly includes an outer layer 33 which contacts the skin of a wearer 44 around the buttocks and crotch area. This layer is made to be smooth and soft so as to be comfortable for the wearer even when fluids such as urine contact this layer and pass therethrough. There is a wick layer 35 which changes color when it is wet so that attendants can see from a distance that a wearer is wet and needs to receive some attention, such as the changing of the liner assembly. Beyond the layer 35 is an absorbent layer 31 formed of a mass of fibers. There is an inner layer 37 which is impervious to fluids so that the fluids such as urine do not wet and/or stain the outer layer of clothing. The liner assembly 36 is held together by soft fiber connectors 38. The liner itself may be removably attached to the basic garment with Velcro so that it is easily removable and changed.

The liners 36 may be constructed to be washable so that they can be reused, or can be made to be disposable. The garment has a belt 42 for holding the garment in place.

The outer layer 33 is made of anti-microbial fiber of the type described in further detail below so that there is protection from microbes and fungus which causes infection and odors.

Layer 33 is made to be a porous fiber material which will draw any moisture from the wearer by wick action away from the wearer's skin and into the absorbent liner. Since the layer 33 is always against the wearer's skin and at least at times is wet from urine, there is the risk of infection which, with the present invention is prevented, due to the layer 33 being constructed of anti-microbial fibers, the construction of which is described in more detail above.

The absorbent material 31 of the liner 36 may also be made of non-woven fibrous material which is also anti-microbial if desired.

Anti-microbial fibers may be made into other products intended for incontinent persons, such as bed linens, and bed packs which are used to prevent bed sores in persons who are confined to bed for extended periods of time. Such products provide a first line of attack against problems caused by microbes especially when used in all areas of the products which come into contact with a person's skin.

Higher loading of the anti-microbial agents (up to 5 times) is used to more effectively act against fungi. This higher loading may be achieved by using various zeolites followed by heating the fiber polymer, e.g. PET, to between 180 and 228 degrees Fahrenheit in hot water which allows further metal loading or ion exchange to replace resident metal ions with another ion or mixture of ions. In addition, this would allow the zeolite at or near the surface of the fiber to be preferentially loaded with the metal ion or mixtures thereof that has the desired biological effect. These methods are particularly useful in reducing costs when expensive metal ions, such as silver, are used in these processes. Also, by adding certain metals, e.g. silver, at this point in the process and not having it present during the high temperature fiber extrusion process, any yellowing or discoloration due to oxidation of the metal ion or its exposure to sulfur and halogens would be greatly reduced.

The invention provides a unique way to use polymers such as PETG to carry and deliver pigments and/or anti-microbial or other additives to a natural fiber, such as cotton, wool, and the like, and generate a final pastel shade fabric without losing the natural fiber's characteristics and/or natural fabric having anti-microbial properties.

PETG is used as a carrier for pigments, such as carbon black, phthalo blue, and the like. It is mixed with other fibers, such as natural fibers, to form a blend, and then the blend is heated, to a temperature of around 140° C. (the PETG can be modified to melt between 90 and 160° C.) either as a separate heating step or during a processing step which includes heating to about temperature. PETG has a melting temperature of around 140° C. (and is available from 90 to 160° C.) and it melts and flows along the fibers with which it is blended. It acts as a binder-carrier in that it forms nodes of color (when a colorant is used) with many points so it looks like a solid color. This provides it with a pastel look. By controlling the amount of colorant added to the PETG there is controllable color values which include pastel shading. PETG has superior wetting ability and therefore it spreads evenly along the other fibers with which it is blended. There are also nodes formed at the intersecting fibers in the blend and there are held together by this characteristic of the PETG. Also, the amount of PETG can be controlled to be small quantities with respect to the other fibers in the blend. Thus, when blended with cotton in this manner, such a blend may properly be characterized as "all cotton" having color and/or anti-microbial (or other) agents, which have been added by the PETG.

Figure 8:
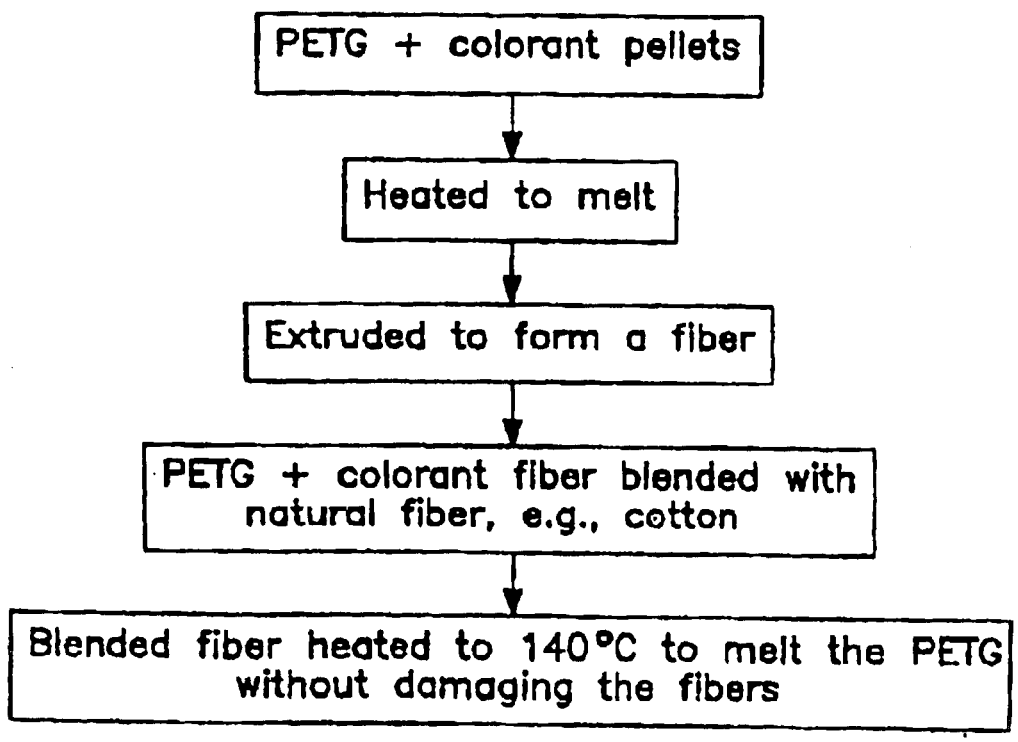
FIG. 8 is a flow chart showing the preparation of the fibers and yarn for use in making a woven or nonwoven fabric.

This can be accomplished in more than one manner. One method is shown in FIG. 8 in which the PETG and colorant pellets are mixed together, after which they are heated to melt and are then extruded to form a PETG fiber with the colorant in it. The PETG is then blended with a natural fiber, such as cotton, to form a blend, which will have the color of the colorant, which the PETG fiber takes on as its color. The cotton is white so that the color taken on is a pastel color. If the colorant is black, then the blend becomes a shade of gray. If desired other fibers can be blended with the PETG fibers, such as silk, flax, polypropylene, polyethylene, wool, polyester, acrylic, nylon, PTT, 3GT, rayon, modified rayon, and acetate.

The PETG is then activated by heating it as a temperature of from about 110° to about 140°. This melts the PETG without harming the fibers with which it has been blended. The PETG carrier melts and wicks along the other fibers, that is the cotton or other base fibers, forming small nodes, but it does not ball up as some polymers do and provides "a drop of glue" (small) to bind the fibers together and leaves behind the encapsulated pigment in the fibers.

This fiber blend is then used to form a yarn with in turn is used to form a fabric. The resulting fabric is a pastel shade fabric without the need of going through a dye bath, and has excellent color fastness from both sunlight and washing. The color is a pastel since there are many tiny drops of the colorant which looks like a solid color to an observer. The color remains fast for in excess of 100 commercial launderings. Since the PETG carrier melted after activation, the blended fibers such as cotton are still considered to be 100% cotton fiber.

Figure 9:
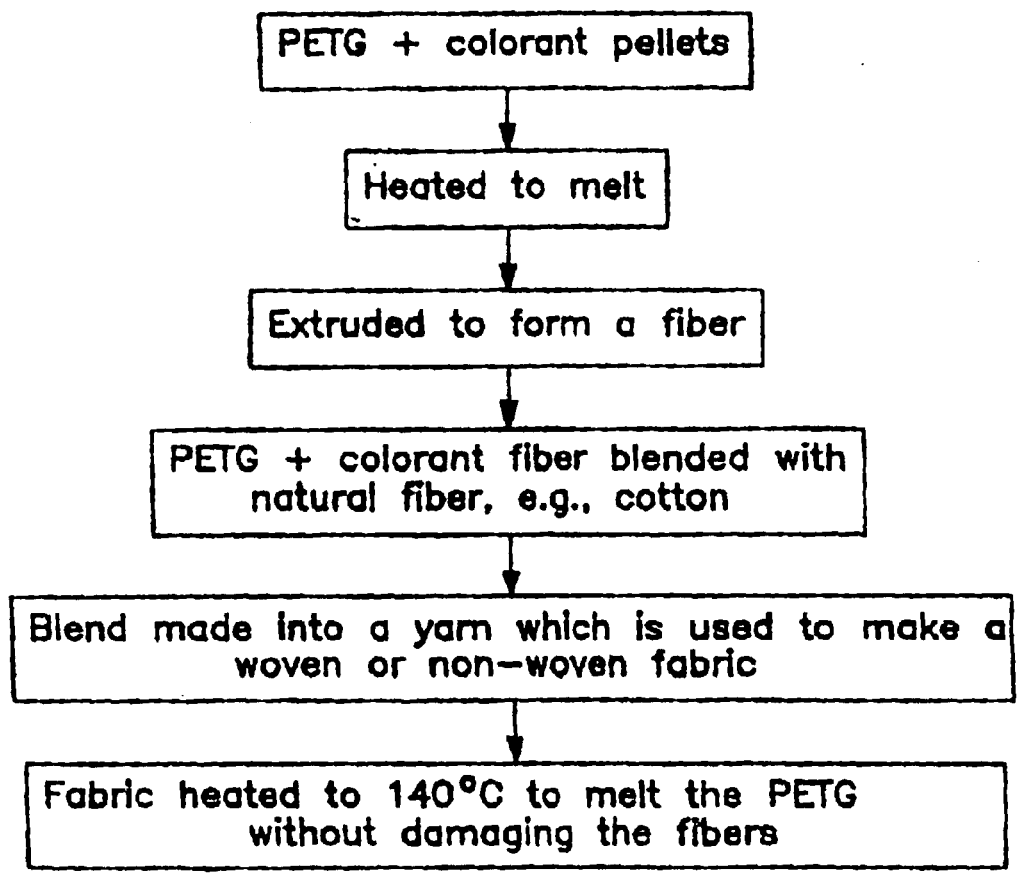
FIG. 9 is a flow chart showing the preparation of fibers and yarn and then of a fabric.
Figure 10:
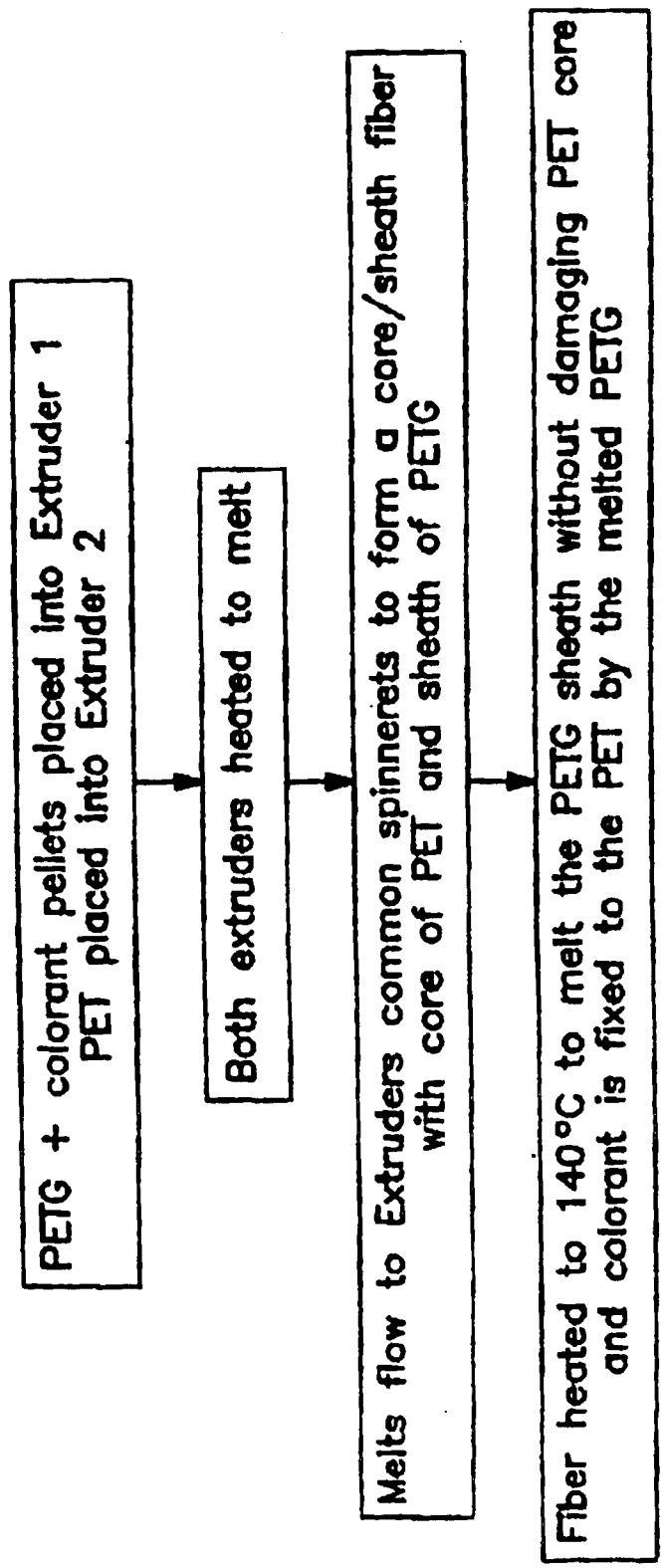
FIG. 10 is a flow chart showing another manner of preparing fibers in accordance with the present invention.

FIG. 9 shows a method similar to that shown in FIG. 10. However, in this process the blended fiber is made into a yarn and the yarn is made into a fabric before the PETG is activated by heating. This heating may be a separate heating step or may take place during the processing of the fabric which may include a heating step for other reasons.

The PETG polymers with anti-microbial additives can be blended with natural fibers such as cotton, silk, flax, and wool, or synthetic fibers such as polyester, polypropylene, polyethylene, acrylic, nylon, PTT, 3GT, rayon, modified rayon, and acetate to make anti-microbial finished fabrics that are able to withstand significant wear and washings and maintain their effectiveness.

A typical example is a fiber using the PETG polymer with the zeolite contained silver additive blended with cotton up to 10% by weight to produce a bed sheet. The binder fiber is activated during the drying cycle of the final bleaching operation or other heat operation. The PETG melts and wets the surface of the cotton fibers to carry the anti-microbial characteristics to the entire sheet with an added benefit of increasing strength and reducing pilling.

The fiber size ranges from 0.7 dTex to 25 dTex and a staple length of 1.0 mm to 180 mm. A continuous filament yarn can also be produced that can be used in a wrap spun application whereby fibers are spun around the anti-microbial filament.

The anti-microbial product withstands more than 50 commercial washings at 80° C. It is immune to UV exposure of at least 225 kj. It possesses excellent abrasion resistance and is unaffected by tests such as Tabor or Wyzenbeek. It is not affected by at least 50 dry cleanings.

FIG. 10 is another flow diagram for an arrangement, which provides a bi-component fiber with a PET core and a PETG sheath containing a desired additive, such as pigment and/or an anti-microbial agent. The PETG and the colorant pellets are placed into a first extruder and PET pellets are placed into a second extruder. Both are heated sufficiently so that the extruders cause the melts to flow to a single spinneret in which the PET is made into the core and the PETG is made into the sheath. In the fiber state, or in a more finished yarn state, or in an even further finished woven or nonwoven fabric state, the fibers are subjected to heat in the vicinity of 140° C. which melts the PETG without harming the PET which has a higher melting point. This heating step provides the benefits of the present invention as discussed above.

Another embodiment involves varying the modulus to create a multi-layer article having a high modulus layer, or a low modulus layer, or anywhere in between. The use of PCT in the a layer provides a hydrolysis resistant surface and resistance to long term washings in boiling water and strong soaps. The multi-layer anti-microbial/anti-fungal synthetic layers can be produced in a wide range of thicknesses.

Additives include pigments, compounds to create a hydrophilic surface, and anti-microbial, anti-fungal, and anti-odor agents. The pigment additives provide uniform colors that do not fade significantly over long-term use and washing, unlike dyes, because these additives are integrally mixed within the polymer making up the sheet or film. In addition, compounds may be used which create a hydrophilic surface. The anti-microbial, anti-fungal and anti-odor additives can be varied, both in types and amounts, depending on the final product desired.

One layer made from low temperature polymers with a melting or softening temperature below 200 degrees C., such as PETG, PE, PP, co-PET, or amorphous PET, may be used as binder carrier for anti-microbial additives.

The anti-microbial additives are inorganic compounds of metals such as copper, tin, zinc, silver, etc. The preferred compound is a zeolite of silver dispersed in PE, PET, or PBT before being added to the layer. The additives could be added directly to the primary polymer with pre-dispersion. The total active ingredients range from 0.1 to 20 percent by sheet weight.

Thus, an anti-microbial sheet material can be produced that is able to withstand significant wear and washings and maintain its effectiveness.

Low melt binder fibers may be blended in at levels of 1 to 20%. The binder fiber can be blended with other fibers such as cotton, wool, polyamides, viscose, flax, acrylic, or polyester. The low melt binder fiber contains levels of the active anti-microbial ingredient ranging from 0.25% to 5%. Fiber properties are from 0.7 denier through 25 denier with cut lengths ranging from 1 mm to 180 mm.

The anti-microbial fibers are used in some embodiments to spin yarn in cotton counts ranging from 4's to 80's. Sheets and pillowcases may be woven or knitted. Yarns used to weave the bed sheets/pillowcases, containing the anti-microbial treated fibers, may be used only in the warp direction, or the filling direction, or may be used in both.

Some sheets and pillowcases have been made using 1–15% anti-microbial fiber in the fabric, which are 1.5–3.5 denier, 1½" staple length and in which 15% of the filling yarn is anti-microbial. For example, they can have 15% anti-microbial fiber, 35% cotton and 50% untreated polyester.

PETG is blended with the cotton, and is heated, it does not ball up but wicks along the other fibers. The cross section becomes thinner as the PETG flows. For loose knit fabrics 15–20% anti-microbial fiber is useful to kill the microbes, whereas for flat woven fabric there can be 10% or less anti-microbial fiber to kill microbes.

The same fabric can be used in bed sheets and for medical scrubs. Woven fabric is desized to remove starch from the warp yarns. High loft batting is used to stuff the mattress pad. 15% of fiber blend is bi-component. In one example, the fiber was made with all PET sheath and core, and was 6½ oz per square yard, 6 denier blended with 6 denier regular while.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A bi-component fiber, comprising:
   (a) as a first component a core of PET having at least 30% and less than 70% of the fiber by weight,
   (b) as a second component a hydrolysis resistant PCT sheath surrounding the core having at least 30% of the fiber by weight and including an additive,
   (c) wherein the said additive comprises an anti-microbial/anti-fungal material in an amount ranging from 0.1% to 70% by weight of the fiber, and (d) wherein the thickness of the sheath is approximately two times the nominal particle size in microns of the additions.

2. The fiber of claim 1, wherein said first component of high tenacity polymer is PET providing strength to the fiber, and said second complement of hydrolysis resistant polymer is PCT providing a hydrolysis resistant surface with good wrinkle resistance, and resistance to long term washings in boiling water and strong soaps.

3. The fiber of claim 2, wherein the core is constructed to have a high modulus with properties of tenacity and elongation similar to cotton.

4. The fiber of claim 2, wherein the core is constructed to have a low modulus with properties similar to wool.

5. The fiber of claim 2, wherein the core is constructed to have an intermediate modulus fiber with properties between cotton and wool.

6. The fiber of claim 1, wherein the additive is hydrophilic to create a fiber that, in a garment, appears to wick body moisture away from the skin and evaporate to create comfort to a wearer.

7. The fiber of claim 1 wherein the additive is pigment to provide uniform colors that do not fade significantly over long-term use and washing.

8. The fiber of claim 1, wherein the fiber size ranges from 0.7 dTex to 25.0 dTex.

9. The fiber of claim 1, wherein said fiber is cut staple in lengths from 1.0 mm to 180.0 mm.

10. The fiber of claim 1, wherein the fiber is continuous filament.

11. The fiber of claim 1, wherein the additive is zeolite of silver.

12. The fiber of claim 1, wherein said sheath is more than 28% of the cross section of the total fiber.

13. The fiber of claim 1, wherein said additive particles are approximately 1 micron cubes and the sheath is approximately 2 microns thick.

14. The fiber of claim 1 wherein the additive comprises a zeolite of a metal selected from the group consisting of silver, zinc, copper and tin.

15. The fiber of claim 1 with one or more further functional additives in said sheath.

* * * * *